US008483829B2

(12) United States Patent
Rochat et al.

(10) Patent No.: US 8,483,829 B2
(45) **Date of Patent: *Jul. 9, 2013**

(54) DYNAMIC REPRESENTATION OF MULTIPOLAR LEADS IN A PROGRAMMER INTERFACE

(71) Applicant: Medtronic, Inc., Minneapolis, MN (US)

(72) Inventors: Marilyn C. Rochat, Golden Valley, MN (US); Arathi Sethumadhavan, Minneapolis, MN (US); Elizabeth A. Schotzko, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/623,288

(22) Filed: Sep. 20, 2012

(65) Prior Publication Data

US 2013/0023948 A1 Jan. 24, 2013

Related U.S. Application Data

(63) Continuation of application No. 13/107,613, filed on May 13, 2011, now Pat. No. 8,355,784.

(51) Int. Cl.
*A61N 1/00* (2006.01)

(52) U.S. Cl.
USPC ........................................................ 607/32

(58) Field of Classification Search
USPC ................................................ 607/32, 116
See application file for complete search history.

(56) References Cited

U.S. PATENT DOCUMENTS

| | | | |
|---|---|---|---|
| 2,956,586 | A | 10/1960 | Zeigler et al. |
| 3,857,399 | A | 12/1974 | Zacouto |
| 3,888,260 | A | 6/1975 | Fischell |
| 3,985,123 | A | 10/1976 | Herzlinger et al. |
| 4,164,946 | A | 8/1979 | Langer |
| 4,262,982 | A | 4/1981 | Kenny |
| 4,397,314 | A | 8/1983 | Vaguine |
| 4,399,820 | A | 8/1983 | Wirtzfeld et al. |
| 4,600,454 | A | 7/1986 | Plummer |

(Continued)

FOREIGN PATENT DOCUMENTS

| | | | |
|---|---|---|---|
| EP | 0659388 | A1 | 6/1995 |
| EP | 1048321 | A2 | 11/2000 |

(Continued)

OTHER PUBLICATIONS

Auricchio et al., "The Pacing Therapies for Congestive Heart Failure (PATH-CHF) Study: Rationale, Design and Endpoints of a Prospective Randomized Multicenter Study" Am J. Cardio., 83:130D-135D, 1999.

(Continued)

*Primary Examiner* — George Manuel
*Assistant Examiner* — Robert N Wieland

(57) ABSTRACT

An external programming system for programming an implantable medical device includes a user display and a memory storing multiple intracardiac lead images. The intracardiac lead images correspond to lead types and includes electrodes spaced according to the spacing of electrodes of a particular lead type. The programmer selects one of the lead images for display based on an indication of which type of lead has been implanted in a patient. The selected image is displayed to a user as part of a graphical user interface for programming cardiac pacing therapy for the patient.

10 Claims, 8 Drawing Sheets

PROGRAMMER 24
10
14
18
20
22
16
30
LV4
LV3
LV2
LV1
32
26
28
12

U.S. PATENT DOCUMENTS 4,603,705 A 8/1986 Speicher et al.
4,628,934 A 12/1986 Pohndorf et al.
4,628,935 A 12/1986 Jones et al.
4,750,494 A 6/1988 King
4,776,334 A 10/1988 Prionas
4,877,032 A 10/1989 Heinze et al.
4,878,898 A 11/1989 Griffin et al.
4,881,410 A 11/1989 Wise et al.
4,902,273 A 2/1990 Choy et al.
5,004,275 A 4/1991 Miller
5,005,613 A 4/1991 Stanley
5,035,246 A 7/1991 Heuvelmans et al.
5,111,816 A 5/1992 Pless et al.
5,113,868 A 5/1992 Wise et al.
5,156,154 A 10/1992 Valenta, Jr. et al.
5,158,536 A 10/1992 Sekins et al.
5,176,619 A 1/1993 Segalowitz
5,188,106 A 2/1993 Nappholz et al.
5,209,238 A 5/1993 Sundhar
5,213,098 A 5/1993 Bennett et al.
5,243,981 A 9/1993 Hudrlick
5,285,744 A 2/1994 Grantham et al.
5,305,745 A 4/1994 Zacouto
5,313,020 A 5/1994 Sackett
5,391,199 A 2/1995 Ben-Haim
5,411,532 A 5/1995 Mortazavi
5,411,537 A 5/1995 Munshi et al.
5,417,717 A 5/1995 Salo et al.
5,419,767 A 5/1995 Eggers et al.
5,423,323 A 6/1995 Orth
5,433,198 A 7/1995 Desai
5,500,006 A 3/1996 Heinze
5,509,411 A 4/1996 Littmann et al.
5,534,018 A 7/1996 Wahlstrand et al.
5,535,752 A 7/1996 Halperin et al.
5,544,656 A 8/1996 Pitsillides et al.
5,549,650 A 8/1996 Bornzin et al.
5,579,234 A 11/1996 Wiley et al.
5,579,764 A 12/1996 Goldreyer
5,591,142 A 1/1997 Van Erp
5,593,430 A 1/1997 Renger
5,628,777 A 5/1997 Moberg et al.
5,662,587 A 9/1997 Grundfest et al.
5,674,258 A 10/1997 Henschel et al.
5,676,153 A 10/1997 Smith et al.
5,683,429 A 11/1997 Mehra
5,713,937 A 2/1998 Nappholz et al.
5,720,768 A 2/1998 Verboven-Nelissen
5,743,267 A 4/1998 Nikolic et al.
5,751,050 A 5/1998 Ishikawa et al.
5,788,647 A 8/1998 Eggers
5,797,903 A 8/1998 Swanson et al.
5,800,460 A 9/1998 Powers et al.
5,800,465 A 9/1998 Thompson et al.
5,810,735 A 9/1998 Halperin et al.
5,814,089 A 9/1998 Stokes et al.
5,836,987 A 11/1998 Baumann et al.
5,873,849 A 2/1999 Bernard
5,902,234 A 5/1999 Webb
5,902,248 A 5/1999 Millar et al.
5,913,814 A 6/1999 Zantos
5,924,997 A 7/1999 Campbell
5,935,084 A 8/1999 Southworth
5,938,690 A 8/1999 Law et al.
5,941,904 A 8/1999 Johnston et al.
5,957,957 A 9/1999 Sheldon
5,999,848 A 12/1999 Gord et al.
6,009,349 A 12/1999 Mouchawar et al.
6,015,386 A 1/2000 Kensey et al.
6,024,704 A 2/2000 Meador et al.
6,032,699 A 3/2000 Cochran et al.
6,033,398 A 3/2000 Farley et al.
6,038,480 A 3/2000 Hrdlicka et al.
6,044,297 A 3/2000 Sheldon et al.
6,058,329 A 5/2000 Salo et al.
6,061,593 A 5/2000 Fischell et al.
6,077,136 A 6/2000 Arai et al.
6,078,830 A 6/2000 Levin et al.
6,081,748 A 6/2000 Struble et al.
6,115,626 A 9/2000 Whayne et al.
6,115,636 A 9/2000 Ryan
6,120,442 A 9/2000 Hickey
6,155,267 A 12/2000 Nelson
6,163,716 A 12/2000 Edwards et al.
6,163,725 A 12/2000 Peckham et al.
6,165,135 A 12/2000 Neff
6,171,252 B1 1/2001 Roberts
6,197,021 B1 3/2001 Panescu et al.
6,197,677 B1 3/2001 Lee et al.
6,206,835 B1 3/2001 Spillman, Jr. et al.
6,206,874 B1 3/2001 Ubby et al.
6,223,080 B1 4/2001 Thompson
6,234,973 B1 5/2001 Meador et al.
6,241,418 B1 6/2001 Suzuki et al.
6,264,606 B1 7/2001 Ekwall et al.
6,277,078 B1 8/2001 Porat et al.
6,287,256 B1 9/2001 Park et al.
6,299,582 B1 10/2001 Brockway et al.
6,301,500 B1 10/2001 Van Herck et al.
6,309,350 B1 10/2001 VanTassel et al.
6,309,385 B1 10/2001 Simpson
6,328,699 B1 12/2001 Eigler et al.
6,358,245 B1 3/2002 Edwards et al.
6,360,123 B1 3/2002 Kimchi et al.
6,363,279 B1 3/2002 Ben-Haim et al.
6,366,811 B1 4/2002 Carlson
6,370,431 B1 4/2002 Stoop et al.
6,406,677 B1 6/2002 Carter et al.
6,421,567 B1 7/2002 Witte
6,438,408 B1 8/2002 Mulligan et al.
6,466,820 B1 10/2002 Juran et al.
6,477,395 B2 11/2002 Schulman et al.
6,477,417 B1 11/2002 Levine
6,484,727 B1 11/2002 Vaska et al.
6,496,730 B1 12/2002 Kleckner et al.
6,580,946 B2 6/2003 Struble
6,584,362 B1 6/2003 Scheiner et al.
6,600,954 B2 7/2003 Cohen et al.
6,611,714 B1 8/2003 Mo
6,618,619 B1 9/2003 Florio et al.
6,628,989 B1 9/2003 Penner et al.
6,666,826 B2 12/2003 Salo et al.
6,675,049 B2 1/2004 Thompson et al.
6,768,924 B2 7/2004 Ding et al.
6,812,796 B2 11/2004 Pryanishnikov et al.
6,885,889 B2 4/2005 Chinchoy
6,934,584 B1 8/2005 Wong et al.
6,978,178 B2 12/2005 Sommer et al.
6,978,184 B1 12/2005 Marcus et al.
6,993,384 B2 1/2006 Bradley et al.
6,994,676 B2 2/2006 Mulligan et al.
7,020,524 B1 3/2006 Bradley
7,047,084 B2 5/2006 Erickson et al.
7,174,218 B1 2/2007 Kuzma
7,200,437 B1 4/2007 Nabutovsky et al.
7,200,439 B2 4/2007 Zdeblick et al.
7,204,798 B2 4/2007 Zdeblick et al.
7,214,189 B2 5/2007 Zdeblick
7,218,968 B2 5/2007 Condie et al.
7,239,916 B2 7/2007 Thompson et al.
7,267,649 B2 9/2007 Zdeblick et al.
7,392,088 B2 6/2008 Dong et al.
7,467,016 B2 12/2008 Colborn
7,561,914 B2 7/2009 Busacker et al.
7,574,259 B1 8/2009 Pei et al.
7,583,998 B2 9/2009 Meyer et al.
7,640,060 B2 12/2009 Zdeblick
7,676,273 B2 3/2010 Goetz et al.
7,680,536 B2 3/2010 Sathaye et al.
7,684,863 B2 3/2010 Parikh et al.
7,713,194 B2 5/2010 Zdeblick
7,792,585 B1 9/2010 Shelchuk
2001/0000187 A1 4/2001 Peckham et al.
2001/0002924 A1 6/2001 Tajima
2001/0025192 A1 9/2001 Gerber et al.
2001/0047138 A1 11/2001 Kokate et al.
2001/0053882 A1 12/2001 Haddock et al.

| | | | |
|---|---|---|---|
| 2002/0026183 | A1 | 2/2002 | Simpson |
| 2002/0040236 | A1 | 4/2002 | Lau et al. |
| 2002/0045921 | A1 | 4/2002 | Wolinsky et al. |
| 2002/0072656 | A1 | 6/2002 | Vantassel et al. |
| 2002/0077568 | A1 | 6/2002 | Haddock |
| 2002/0077673 | A1 | 6/2002 | Penner et al. |
| 2002/0095196 | A1 | 7/2002 | Linberg |
| 2002/0099419 | A1 | 7/2002 | Cohen et al. |
| 2002/0111560 | A1 | 8/2002 | Kokate et al. |
| 2002/0120186 | A1 | 8/2002 | Keimel |
| 2002/0151816 | A1 | 10/2002 | Rich et al. |
| 2002/0156417 | A1 | 10/2002 | Rich et al. |
| 2002/0161307 | A1 | 10/2002 | Yu et al. |
| 2002/0169445 | A1 | 11/2002 | Jain et al. |
| 2002/0193859 | A1 | 12/2002 | Schulman et al. |
| 2003/0078623 | A1 | 4/2003 | Weinberg et al. |
| 2003/0105496 | A1 | 6/2003 | Yu et al. |
| 2003/0153952 | A1 | 8/2003 | Auricchio et al. |
| 2003/0191502 | A1 | 10/2003 | Sharma et al. |
| 2004/0024440 | A1 | 2/2004 | Cole |
| 2004/0039417 | A1 | 2/2004 | Soykan et al. |
| 2004/0093053 | A1 | 5/2004 | Gerber et al. |
| 2004/0097965 | A1 | 5/2004 | Gardeski et al. |
| 2004/0098074 | A1 | 5/2004 | Erickson et al. |
| 2004/0143154 | A1 | 7/2004 | Lau et al. |
| 2004/0193021 | A1 | 9/2004 | Zdeblick et al. |
| 2004/0199235 | A1 | 10/2004 | Younis |
| 2004/0215049 | A1 | 10/2004 | Zdeblick et al. |
| 2004/0220637 | A1 | 11/2004 | Zdeblick et al. |
| 2004/0254483 | A1 | 12/2004 | Zdeblick et al. |
| 2004/0260346 | A1 | 12/2004 | Overall et al. |
| 2005/0027320 | A1 | 2/2005 | Nehls et al. |
| 2005/0054892 | A1 | 3/2005 | Lau et al. |
| 2005/0102011 | A1 | 5/2005 | Lau et al. |
| 2005/0246004 | A1 | 11/2005 | Cameron et al. |
| 2005/0267542 | A1 | 12/2005 | David et al. |
| 2006/0020314 | A1* | 1/2006 | Bodner ........................ 607/116 |
| 2006/0058588 | A1 | 3/2006 | Zdeblick |
| 2006/0074454 | A1 | 4/2006 | Freeberg |
| 2006/0122678 | A1 | 6/2006 | Olsen et al. |
| 2006/0161211 | A1 | 7/2006 | Thompson et al. |
| 2006/0247539 | A1 | 11/2006 | Schugt et al. |
| 2006/0265038 | A1 | 11/2006 | Hagen et al. |
| 2007/0100399 | A1 | 5/2007 | Parramon et al. |
| 2007/0123944 | A1 | 5/2007 | Zdeblick |
| 2007/0172896 | A1 | 7/2007 | Goueli et al. |
| 2007/0179569 | A1 | 8/2007 | Zdeblick |
| 2007/0198066 | A1 | 8/2007 | Greenberg et al. |
| 2007/0203537 | A1 | 8/2007 | Goetz et al. |
| 2007/0203544 | A1 | 8/2007 | Goetz et al. |
| 2007/0219591 | A1 | 9/2007 | Zdeblick et al. |
| 2007/0219608 | A1 | 9/2007 | Swoyer et al. |
| 2007/0255336 | A1 | 11/2007 | Herbert et al. |
| 2007/0255373 | A1 | 11/2007 | Metzler et al. |
| 2007/0255460 | A1 | 11/2007 | Lopata |
| 2008/0007186 | A1 | 1/2008 | Lu et al. |
| 2008/0021292 | A1 | 1/2008 | Stypulkowski |
| 2008/0027289 | A1 | 1/2008 | Zdeblick |
| 2008/0027514 | A1 | 1/2008 | DeMulling et al. |
| 2008/0039916 | A1 | 2/2008 | Colliou et al. |
| 2008/0045826 | A1 | 2/2008 | Greenberg et al. |
| 2008/0058656 | A1 | 3/2008 | Costello et al. |
| 2008/0061630 | A1 | 3/2008 | Andreu et al. |
| 2008/0091246 | A1 | 4/2008 | Carey et al. |
| 2008/0097227 | A1 | 4/2008 | Zdeblick et al. |
| 2008/0097566 | A1 | 4/2008 | Colliou |
| 2008/0114230 | A1 | 5/2008 | Addis |
| 2008/0140141 | A1 | 6/2008 | Ben-David et al. |
| 2008/0140167 | A1 | 6/2008 | Hagen et al. |
| 2008/0147168 | A1 | 6/2008 | Ransbury et al. |
| 2008/0154328 | A1 | 6/2008 | Thompson et al. |
| 2008/0154340 | A1 | 6/2008 | Goetz et al. |
| 2008/0163097 | A1 | 7/2008 | Goetz et al. |
| 2008/0167702 | A1 | 7/2008 | Ransbury et al. |
| 2008/0177343 | A1 | 7/2008 | Dal Molin et al. |
| 2008/0183256 | A1 | 7/2008 | Keacher |
| 2008/0215118 | A1 | 9/2008 | Goetz et al. |
| 2008/0255647 | A1 | 10/2008 | Jensen et al. |
| 2008/0294062 | A1 | 11/2008 | Rapoport et al. |
| 2008/0294218 | A1 | 11/2008 | Savage et al. |
| 2008/0306394 | A1 | 12/2008 | Zdeblick et al. |
| 2008/0312726 | A1 | 12/2008 | Frank et al. |
| 2009/0018632 | A1 | 1/2009 | Zdeblick et al. |
| 2009/0024184 | A1 | 1/2009 | Sun et al. |
| 2009/0043352 | A1 | 2/2009 | Brooke et al. |
| 2009/0054946 | A1 | 2/2009 | Sommer et al. |
| 2009/0054947 | A1 | 2/2009 | Bourn et al. |
| 2009/0062880 | A1 | 3/2009 | Li et al. |
| 2009/0196471 | A1 | 8/2009 | Goetz et al. |
| 2009/0196472 | A1 | 8/2009 | Goetz et al. |
| 2009/0287266 | A1 | 11/2009 | Zdeblick |
| 2009/0299447 | A1 | 12/2009 | Jensen et al. |
| 2010/0016928 | A1 | 1/2010 | Zdeblick et al. |
| 2010/0137935 | A1 | 6/2010 | Parikh et al. |
| 2010/0152801 | A1 | 6/2010 | Koh et al. |
| 2010/0204766 | A1 | 8/2010 | Zdeblick et al. |
| 2010/0268059 | A1 | 10/2010 | Ryu et al. |
| 2011/0004264 | A1 | 1/2011 | Siejko et al. |
| 2012/0123496 | A1 | 5/2012 | Schotzko et al. |

FOREIGN PATENT DOCUMENTS

| | | | |
|---|---|---|---|
| EP | 1050265 | A2 | 11/2000 |
| EP | 1136033 | A1 | 9/2001 |
| EP | 1266606 | A2 | 12/2002 |
| EP | 1321097 | A2 | 6/2003 |
| EP | 1426079 | A2 | 6/2004 |
| EP | 1938861 | A1 | 7/2008 |
| JP | 6456031 | | 2/1989 |
| JP | 2099036 | | 4/1990 |
| JP | 3055032 | | 3/1991 |
| JP | 5269136 | | 10/1993 |
| JP | 2000139833 | | 5/2000 |
| JP | 2002272758 | | 9/2002 |
| WO | WO 99/52588 | A1 | 10/1999 |
| WO | WO 01/43821 | A1 | 6/2001 |
| WO | WO 01/95787 | A2 | 12/2001 |
| WO | WO 02/053228 | A1 | 7/2002 |
| WO | WO 02/065894 | A2 | 8/2002 |
| WO | WO 2004/020040 | A2 | 3/2004 |
| WO | WO 2004/052182 | A2 | 6/2004 |
| WO | WO 2004/066814 | A2 | 8/2004 |
| WO | WO 2004/066817 | A2 | 8/2004 |
| WO | WO 2004/067081 | A2 | 8/2004 |
| WO | WO 2006/029090 | A2 | 3/2006 |
| WO | WO 2006/042039 | A2 | 4/2006 |
| WO | WO 2006/069322 | A2 | 6/2006 |
| WO | WO 2006/073915 | A2 | 7/2006 |
| WO | WO 2006/105474 | A2 | 10/2006 |
| WO | WO 2007/005641 | A2 | 1/2007 |
| WO | WO 2007/075974 | A2 | 7/2007 |
| WO | WO 2007/120884 | A2 | 10/2007 |
| WO | WO 2007/149546 | A2 | 12/2007 |
| WO | WO 2008/004010 | A2 | 1/2008 |
| WO | WO 2008/008755 | A1 | 1/2008 |
| WO | WO 2008/027639 | A2 | 3/2008 |
| WO | WO 2009/131749 | A2 | 10/2009 |
| WO | 2009/134475 | | 11/2009 |
| WO | 2009/137121 | | 11/2009 |

OTHER PUBLICATIONS

Borky et al., "Integrated Signal Conditioning for Silicon Pressure Sensors" IEEE Transactions on Electron Devices ED-26(12): 1906-1910, 1979.

Little et al., "The Output of the Heart and its Control" Physiology of the Heart and Circulation, $4^{th}$ ed., Year Book Medical Publishers Inc. pp. 165-187, 1989.

Paolocci et al., "Positive Inotropic ad Lusitropic Effects of HNO/NO in failing hearts: Independence from B-adrenergic signaling" PNAS vol. 100, No. 9, pp. 5537-5542, 2003.

Receveur et al., "Laterally Moving Bistable MEMS DC-Switch for Biomedical Applications," Journal of Microelectromechanical Systems, vol. 14, No. 5, Oct. 2005.

U.S. Appl. No. 12/909,057, by Wade M. Demmer, filed Oct. 21, 2010.

U.S. Appl. Application No. 12/395,538, by Bi et al., filed Feb. 27, 2009.

United States Patent Application No. Elizabeth A. Schotzko, filed Sep. 29, 2010.

(PCT/US2012/037525) Notification of Transmittal of the International Search Report and the Written Opinion of the International Searching Authority, Mailed Sep. 11, 2012, 11 pages.

* cited by examiner 140a
20a
Tip
LV1
LV2
LV3
LV4
18a
RVcoil
Can
16a 140b
20b
Tip
LV1
LV2
LV3
LV4
18b
RVcoil
Can
16b

DYNAMIC REPRESENTATION OF MULTIPOLAR LEADS IN A PROGRAMMER INTERFACE

TECHNICAL FIELD

The invention relates to programming of implantable medical devices and, more particularly, to representation of cardiac leads in the user interface of a programmer

BACKGROUND

Implantable medical devices (IMD), such as pacemakers or other cardiac devices, may be used to deliver electrical stimulation therapy to a patient's heart to treat a variety of symptoms or conditions, such as heart failure and arrhythmia. In general, an IMD delivers cardiac stimulation therapy in a form of electrical pulses. An IMD may deliver cardiac stimulation therapy via one or more leads that include one or more electrodes located within in or proximate to the heart.

In general, a physician selects values for a number of programmable parameters in order to define the electrical cardiac stimulation therapy to be delivered by the IMD to a patient. For example, the physician ordinarily selects a combination of electrodes carried by one or more implantable leads, and assigns polarities to the selected electrodes. In addition, the physician may select an amplitude, which may be a current or voltage amplitude, and a pulse width for stimulation pulses to be delivered to the patient. The physician may also select chambers of the heart to which therapeutic stimulation should be delivered, select a mode of cardiac pacing, select a progression of anti-tachyarrhythmia therapies, and select values for a number of other programmable parameters, such as escape, atrioventricular, or inter-ventricular intervals.

SUMMARY

In general, the disclosure is directed to the depiction of multipolar intracardiac leads including an electrode spacing/location configuration. In some examples, the intracardiac leads depicted are quadripolar leads. In some examples, a programming device receives an indication of a type of lead, depicts one of a plurality of lead images having different electrode configurations based on the selected type. By displaying a lead image with a more accurate representation of the electrode configuration of the actual lead implanted in the patient, a programmer may facilitate more efficient programming of vectors for stimulation or sensing by a user.

In one example, the disclosure is directed to a method including retrieving, from a memory storing a plurality of intracardiac lead images, a selected lead image, the lead image selected based on an indication of a lead type, and displaying the selected lead image, wherein the selected lead image includes a plurality of electrodes spaced according to spacing of electrode on the lead type.

In another example, the disclosure is directed to a system including a user display, a memory configured to store a plurality of intracardiac lead images, each of the lead images associated with a respective one of a plurality of lead types, and each of the lead images including a plurality of electrodes spaced according to the spacing of electrodes of the associated lead type, an interface configured to receive an indication of which of the plurality of lead types corresponds to a lead of a patient, and a processor configured to choose the one of the lead images that is associated with the indicated lead type, and provide the chosen image to the user display for display as part of a graphical user interface for programming cardiac pacing therapy for the patient.

In another example, the disclosure is directed to a system including means for receiving an indication of a lead type, means for retrieving a lead image selected based on the indication of lead type from a plurality of intracardiac lead images, and means for displaying the selected lead image, wherein the selected lead image includes a plurality of electrodes spacing according to spacing of electrodes on the lead type.

The details of one or more examples are set forth in the accompanying drawings and the description below. Other features, objects, and advantages will be apparent from the description and drawings, and from the claims.

DETAILED DESCRIPTION

Figure 1:
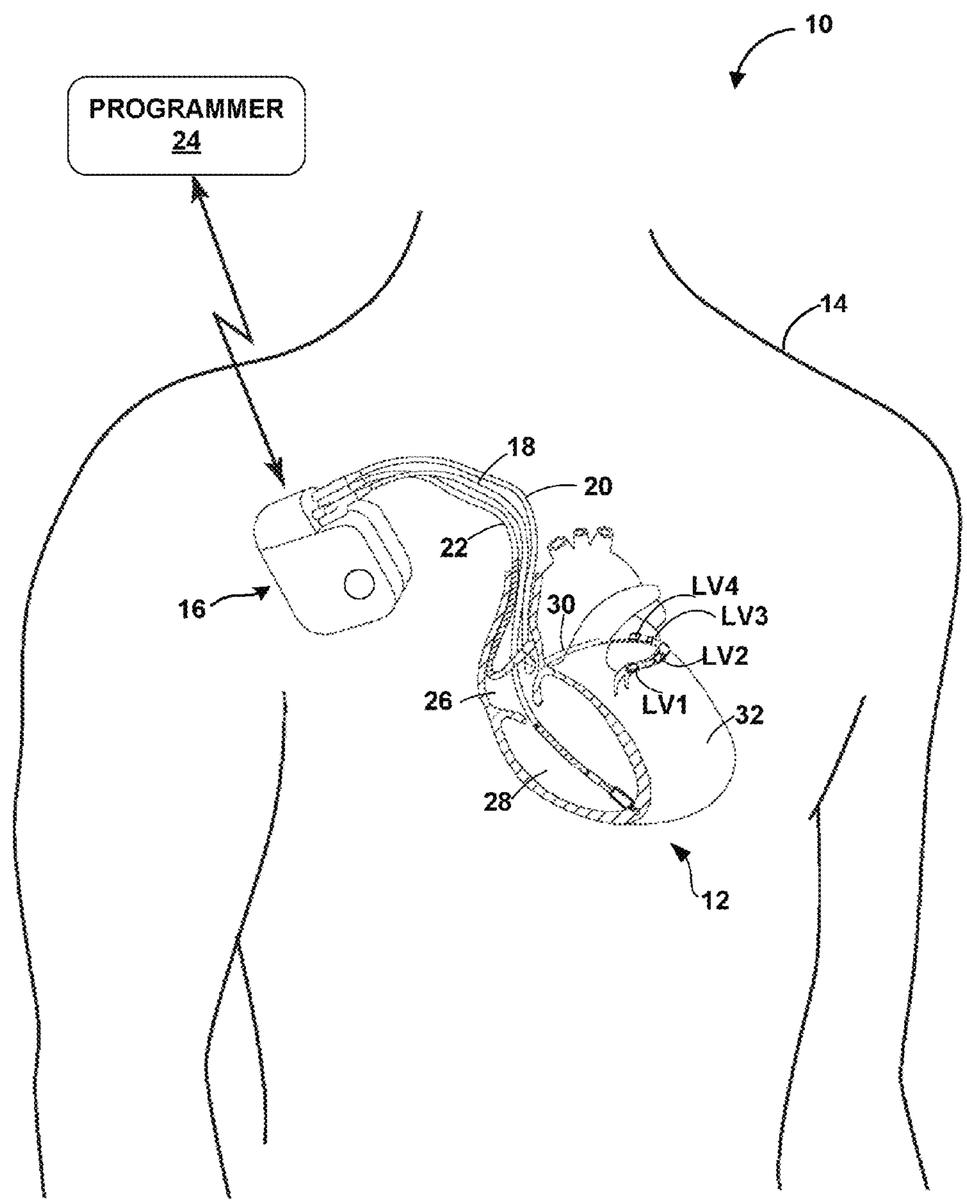
FIG. 1 is a conceptual diagram illustrating an example system that provides therapeutic electrical stimulation to the heart of a patient.

In various examples consistent with this disclosure, an implantable medical device (IMD) intended to provide pacing or other cardiac stimulation, as well as sense electrical activity of the heart, may be implanted within a patient. The IMD may be coupled to a number of leads that extend into and around the patient's heart. Each of the leads may include any number of electrodes. Leads with multiple electrodes may be referred to as multipolar leads.

Two or more electrodes on one or more of the leads may cooperate to provide stimulation at a particular location or region of tissue. A "vector" for stimulating the location or region may refer to the two or more electrodes, as well as the polarity of the electrodes or resulting direction of the stimulation. The various electrodes on the leads may be programmed individually to provide stimulation at a number of different locations and with a variety of vectors. Similarly, two or more electrodes on one or more of the leads that cooperate to sense electrical activity, e.g., from a particular chamber of heart, may be referred to as a sensing vector.

In some examples, one or more of the cardiac leads implanted within the patient is a left ventricular (LV) quadripolar lead. The LV quadripolar lead provides a total of four electrodes and the capability to program all four electrodes as a cathode or an anode. This flexibility in programming provides numerous possible LV vectors, each of which includes at least one electrode configured as an anode and at least one electrode configured as a cathode. In some examples, vectors including two or more anodes or two or more cathodes, resulting in greater anodal and/or cathodal surface area, are used. A physician that has implanted the LV quadripolar lead may want to test one or more of the potential vectors to determine which of the numerous vectors is most effective for the patient.

The sixteen or more vector choices provided by an LV quadripolar lead result in a relatively complex vector selection process when an LV quadripolar lead is implanted. In addition, different multipolar lead models may have a variety of different spacings between the electrodes, e.g., spacings between the four electrodes of a quadripolar lead. The size, shape and/or location of the electrical field resulting from delivery of an electrical stimulation via a vector may vary based on the spacing of the electrodes on a multipolar lead, and thus the spacing between the electrodes of the vector. It may be helpful to a clinician to have an accurate depiction of the type of multipolar lead, e.g., quadripolar LV lead, implanted in a patient, with an accurate depiction of the spacing between the electrodes of the lead, i.e., the positions of the electrodes on the lead. The depiction may influence the choice of a vector, and the order in which vectors are tested. In some examples, the multipolar lead may have more or less the four electrodes of a quadripolar lead. For example, a lead may have three or five electrodes.

In order for a programmer user interface to show a graphical depiction of an implanted lead with appropriate electrode positions and spacing, a user may choose an appropriate graphic corresponding to the multipolar lead model that has been implanted. In some examples, the user may select a graphic from a number of graphics stored within the programmer based on an image that represents the graphic. In some examples the multipolar lead may include four electrodes. In other examples the multipolar lead may include more or less electrodes. For example, a lead may include 3 or 5 electrodes. The graphic displayed on the user interface may include the appropriate number of electrodes, as well as appropriate positioning and spacing of the electrodes. Many of the examples below refer to a quadripolar lead; however, the examples may be applicable to multipolar leads with any number of electrodes greater than one.

In some examples, the user may select a graphic by providing a lead model or serial number. For example, the user may manually input the lead model or serial number. In other examples, the programmer may be coupled to a scanner. The scanner may read a barcode, radiofrequency identification (RFID) tag, or another identification element from on the lead or a lead package. In other examples, the scanner may scan a patient identification element, which may itself indicate the type of lead that has been implanted, or may provide a patient identification that allows the type of lead that has been implanted to be retrieved from database of patient information.

The user may then program the therapeutic stimulation and sensing for the patient, e.g., choose electrodes for one or more vectors to test. The graphic of the lead may be modified to depict the selection. For example, the graphic may highlight the electrodes chosen, as well as indicate whether the chosen electrode is being programmed as an anode or a cathode. In some examples, the graphic may be modified to depict the resulting vector as well.

In some examples, a user may choose a graphic that includes an electrode configuration that approximates the electrode configuration of an implanted lead. The user may select from a set of graphics including common electrode spacing configurations. For example, a programmer may present lead images with a variety of electrode spacing configurations including dual tight electrodes, where there are two electrodes close together near the tip, and a second set of electrodes close together at a distance away from the electrodes close to the tip. Another lead image may depict an electrode configuration with a tight middle spacing. Such an electrode spacing configuration may include an electrode near the tip of the electrodes, a space, two electrodes close together, another space and the fourth electrode. Another lead image may depict an electrode spacing configuration with equal spacing between the four electrodes. Another lead image may depict an electrode spacing configuration where there are two electrodes closely spaced near the tip and then the other two electrodes have a greater space between each other and between them and the first two electrodes. Another lead image may depict an electrode spacing configuration with wide unequal spacing between the four electrodes. For example, in a quadripolar lead including electrodes LV1-LV4, the electrodes may be spaced to such that there are 10 millimeters (mm) between LV1 and LV2, 20 mm between LV2 and LV3 and 15 mm between LV3 and LV4.

In some examples, the user may also be able to modify the electrode spacing. For example, a user may select from among a plurality of predefined lead images that approximate most multipolar lead electrode spacing configurations. The user may then select one or more of the electrodes and move it on the lead image to provide a better approximation of the configuration of the actual lead implanted within the patient.

In some examples, a programmer may have a default display of equal spacing between the electrodes. The user may modify the spacing to approximate the spacing of the electrodes of the lead implanted within the patient. In some examples the user may be able to save a lead image with the modified spacing in order to retrieve the lead image for use when the same lead type has been used in another patient.

In some examples, a lead image may include features in addition to the electrode spacing configuration. For example, the lead image may depict whether the lead that was implanted was a straight or canted lead. In some examples, the lead image may also include a depiction of the location of fixation points, e.g., a depiction of the type, such as structure, and location of a fixation mechanism. Although the examples below are discussed primarily with respect to programming of LV quadripolar leads, other multipolar leads, such as atrial or RV leads, with the same or a different number of electrodes, may also be programmed.

FIG. 1 is a conceptual diagram illustrating an example system 10 that provides electrical stimulation to heart 12 of patient 14. System 10 includes implantable medical device (IMD) 16, which is connected to leads 18, 20, and 22, and is communicatively coupled to a programmer 24. IMD 16 senses electrical signals attendant to the depolarization and repolarization of heart 12, e.g., a cardiac electrogram (EGM), via electrodes on one or more leads 18, 20 and 22 or the housing of IMD 16. IMD 16 may also deliver therapy in the form of electrical signals to heart 12 via electrodes located on one or more leads 18, 20 and 22 or a housing of IMD 16. The therapy may be pacing, cardioversion and/or defibrillation, which may be delivered in the form of electrical pulses. IMD 16 may similarly include or be couple to other sensors, such as one or more accelerometers, for detecting other physiological parameters of patient 14, such as activity or posture.

Leads 18, 20, 22 are intracardiac leads that extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. In some examples, LV lead 20 is a quadripolar lead with electrodes LV1-LV4. Right atrial (RA) lead 22 extends through one or more veins and the vena cava, and into the right atrium 26 of heart 12.

In some examples, programmer 24 takes the form of a handheld computing device, computer workstation or networked computing device that includes a user interface for presenting information to and receiving input from a user. A user, such as a physician, technician, surgeon, electro-physiologist, or other clinician, may interact with programmer 24 to retrieve physiological or diagnostic information from IMD 16. A user may also interact with programmer 24 to program IMD 16, e.g., select electrodes through which to apply electrical stimulation. The user interface may include a display that allows the user to visualize the electrode spacing configuration of the lead 20 that has been implanted, for example.

IMD 16 and programmer 24 may communicate via wireless communication using any techniques known in the art. Examples of communication techniques may include, for example, low frequency or radiofrequency (RF) telemetry. Other techniques are also contemplated. In some examples, programmer 24 may include a programming head that may be placed proximate to the patient's body near the IMD 16 implant site in order to improve the quality or security of communication between IMD 16 and programmer 24. In some examples, programmer 24 may be located remotely from IMD 16, and communicate with IMD 16 via a network. Programmer 24 may also communicate with one or more other external devices using a number of known communication techniques, both wired and wireless.

Figure 2:
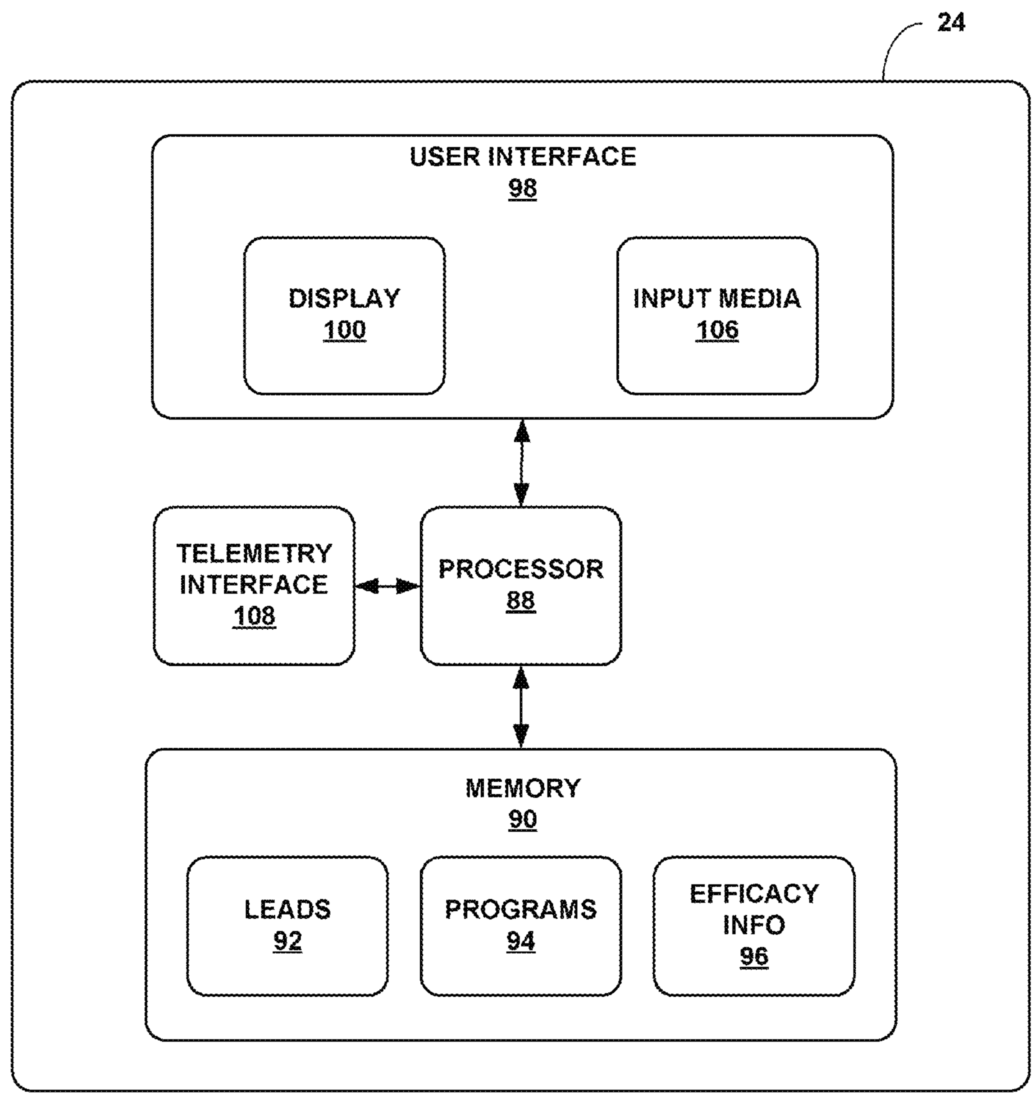
FIG. 2 is a conceptual diagram illustrating an example programmer for programming an implantable medical device.

FIG. 2 is a conceptual diagram illustrating an example programmer 24 for programming IMD 16. In the example of FIG. 2, programmer 24 includes processor 88, memory 90, telemetry interface 108 and user interface 98. In general, a user, i.e., a physician or clinician uses programmer 24 to program and control IMD 16.

In the example of FIG. 2, memory 90 stores images of a variety of leads 92. The lead images include an array of electrode spacing options. In some examples, leads 92 stores images of lead combinations as well. For example, leads 92 may store multiple images including the same electrode spacing configuration on LV lead 20, each with a different RV lead 18. RV lead 18 may have one or more of an RV tip electrode, an RV ring electrode and an RV coil electrode.

In some examples, the lead images are identified in leads 92 by lead name or serial number. In some examples, the lead images are identified in leads 92 by approximate electrode spacing. In some examples, the lead images are stored in a directory structure or the like based on approximate electrode spacing. For example, leads having even electrode spacing may be stored together, leads having a close spacing near the lead tip may be stored together, and leads having a close center spacing may be stored together.

Memory 90 may store program 94 including operational parameters that specify possible therapy and sensing parameters for download to IMD 16. As examples, therapy parameters may include pulse width and amplitude for pacing pulses, as well as values for various intervals that control the delivery or non-delivery, and the timing, of pacing pulses. Memory 90 may also store program instructions that, when executed by processor 88, control processor 88 and programmer 24 to provide the functionality ascribed to them herein. Memory 90 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Memory 90 may comprise a tangible computer-readable storage medium, e.g., a non-transitory medium.

Memory 90 may also record efficacy information 96 for particular programs 94 in combination with information identifying the electrodes selected by a user for a particular lead 92, e.g., the vector selected for the delivery of therapeutic stimulation. In some examples processor 88 may determine the efficacy of a particular electrode combination, e.g., vector, based on cardiac signals received from IMD 16 via telemetry interface 108. In some examples the cardiac signals may be electrogram (EGM) signals. In some examples the cardiac signals may be heart sounds-based signals. In some examples, the efficacy information 96 may include information received from the user. For example, the user may provide information regarding previous results using a particular electrode grouping. In this manner, over time different electrode groupings for a particular lead type may be rated in terms of efficacy so that the user ultimately may select an effective electrode combination and stimulation parameters. Over time, the programmer 24 may be able to suggest electrode combinations based on previous outcomes.

A user interacts with processor 88 via user interface 98 in order to identify a lead image that corresponds to the lead implanted within patient 14. The user also interacts with the user interface to select an electrode or electrode combination to provide stimulation. Processor 88 may provide display 100, i.e., a graphical user interface (GUI), via user interface 98 to facilitate interaction with the user. Processor 88 may include a microprocessor, a microcontroller, a DSP, an ASIC, an FPGA, or other equivalent discrete or integrated logic circuitry. The user interface 98 may include display 100 and one or more input media 106. In addition, the user interface may include lights, audible alerts, or tactile alerts.

The programmer 24 may include a number of input media 106. In some examples, programmer 24 may include a keyboard. In some examples, the input media 106 may include a barcode scanner. In some examples, the input media 106 may be a touch screen.

In some examples, processor 88 may control IMD 16 via telemetry interface 108 to test selected electrode combination by controlling a stimulator within IMD 16 to deliver cardiac stimulating pulses to heart 12 via the selected electrode combinations. In particular, processor 88 transmits programming signals to IMD 16 via telemetry interface 108.

After completion of electrode testing, processor 88 may transmit the operational parameters, e.g., vector(s), selected by the physician to IMD 16 via telemetry interface 108 for storage in the IMD 16. The selected vectors may be used to deliver therapy chronically or over an extended period of time.

Programmer 24 may be provided in the form of a handheld device, portable computer or workstation that provides a user interface to a physician or patient. The physician interacts with user interface 98 to program stimulation parameters for IMD 16 via external programmer 24.

Figure 3:
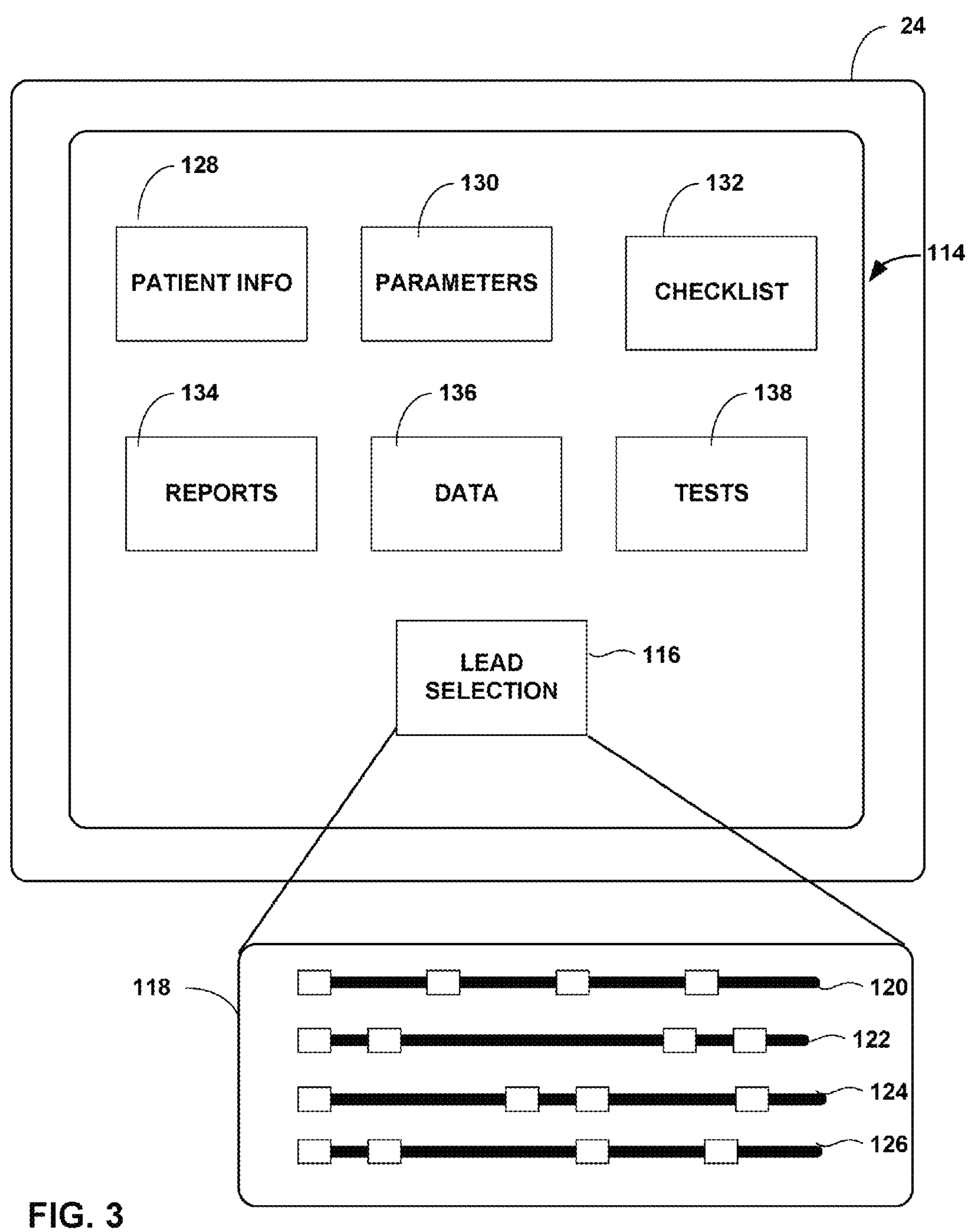
FIG. 3 is a schematic diagram illustrating an example user interface presented by the example programmer of FIG. 2.

FIG. 3 is a schematic diagram illustrating an example user interface that may be presented by example of programmer 24 of FIG. 2. Screen 114 is an example GUI that may be presented by user interface 98 of FIG. 2, which may provide a number of different screens and interactive possibilities. For example, user interface 98 may include a touch screen, and a physician may be able to make selections using a finger or other pointing device. Screen 114 may be a "home" or start screen for example. Screen 114 may include a number of icons that lead to additional screens. The additional screens may present information, programming capabilities, or both.

In response to selection of lead selection function 116, e.g., via a shortcut or other interactive element on screen 114, programmer 24 may present a lead selection screen similar to screen 118. In some examples, lead selection screen 118 may be a pull-down screen or pop-up screen that appears along with the icons of screen 114. In some examples, lead selection screen 118 may replace home screen 114.

In the example of FIG. 3, screen 118 includes lead images 120, 122, 124 and 126. Lead image 120 depicts a lead including wide, even spacing between the four electrodes of a quadripolar lead. Lead image 122 depicts a quadripolar lead including double short spacing. That is, two electrodes close together near the tip of the lead and two electrodes close together a distance away from the tip. Lead image 124 depicts a quadripolar lead with short middle spacing of the electrodes. That is, a lead with an electrode at the tip, a large space, two electrodes close together, and another large space. Lead image 126 depicts a quadripolar lead having a short tip spacing. That is, a lead with an electrode at the tip and another electrode close to the tip electrode with a large space before the next electrode, and another large space before the final electrode.

In some examples, a physician may select a lead image showing electrode spacing that approximately corresponds to the electrode spacing of the lead implanted in patient 14 based on the images on lead selection screen 118. In some examples, lead selection screen 118 may be an intermediate screen between the home screen 114 and a selection screen that includes a number of lead images that correspond to actual leads that may be implanted in a patient 14. Each of the lead images 120, 122, 124 and 126 may lead to a display screen including lead images with approximately the same lead spacing as those depicted on screen 118. In some instances the lead images may include not only the approximate lead spacing of the lead the image represents, but a final fixation configuration. For example, the lead images may depict a canted lead, or the placement of fixation points. In some examples the lead images may be associated with a lead model name or serial number. In some examples, after a lead image has been chosen, a user may then select one or more of the electrodes depicted to use when delivering cardiac electrical stimulation. The image of the lead including the relative spacing of the electrodes as implanted in the patient may be helpful to a physician in determining which electrodes to test first.

Screen 114 may include one or more of the icons 128, 130, 132, 134, 136, and 138. In some examples patient information 128 may include information regarding a patient including, for example, patient name, history, date of birth, hospital ID, the types of leads implanted, the type of stimulation that is to be provided, or the patient diagnosis. In some examples choosing parameters 130 brings a user to a screen that allows the user to program various therapy and sensing parameters, including selecting vectors for delivery of therapeutic stimulation and sensing. In some examples, if a lead image has been selected from the lead selection screen 118, the screen displayed in response to the user selecting parameters 130 may include the lead image selected to enable a user to select desired electrodes or electrode combinations for vector programming In some examples a lead image may indicate which electrodes have been selected. In some examples, the image may include an indication of a stimulation or sensing, e.g., pacing, vector resulting from the electrodes selected.

After an electrode has been selected and pacing parameters have been set, a physician may test the chosen parameters. These tests may be done by selecting the tests 138 icon, for example. In some examples, the test icon brings up a display screen that allows a user to select from one or more preprogrammed tests sequences. In some examples, the test results may be displayed. In some examples, the screen may display an EGM signal as the test is being conducted.

In some examples, the display screen 114 may also include icons for reports 134, data 136 and a checklist 132. Checklist 132 may include a checklist to ensure that appropriate tests of IMD 16 are completed. In some examples, checklist 132 may include a checklist to ensure that a predetermined number of vectors have been tested. In some examples, the checklist 132 may include a checklist for a clinic to ensure all tasks associated with the patient are completed before discharge. Selection of checklist 132 may result in display of a graphical user interface that includes a number of checklists. Some of the checklists may be related to programming IMD 16, while other checklists may be related to overall patient care.

In some examples, selection of data 136 may result in user interface 98 displaying patient diagnostic data or data associated with the integrity of the system. In some examples data 136 may include a list of various type of data associated with the IMD 16 and the patient 12. For example, data 136 may include data relating to trends regarding impedance, sensing, or capture threshold trends.

In some examples, display screen 114 may also include reports 134. Selecting reports 134 may result in a display screen including a variety of reports that may be generated by programmer 24. The reports may include, for examples, report related to patient diagnostics, efficacy of a chosen vector over time, the integrity of the system, changes in efficacy of provided stimulation since previous programming, patient clinical data, patient information or changes made during a follow-up session FIGS. 4A-4D are schematic diagrams illustrating example lead images 140*a*-140*d* that may be presented by user interface 98 as part of a programming screen in response selection of one of lead images 140*a*-140*d* and selection of programming interface such as tests screen 138 or parameters screen 130 from home screen 114. The lead image 140 includes an image of IMD 16 connected to a LV lead 20 and RV lead 18. LV lead 20 includes four electrodes LV1-LV4. RV lead 18 includes a single electrode, RV coil. In some examples, not shown, RV lead 18 may include one or more of an RV tip electrode, an RV ring electrode and an RV coil electrode. Due to the number of electrodes on quadripolar lead 20, there are a number of possible electrode combinations, or vectors, for the application of stimulation to or sensing of the heart 12. Each of the electrodes LV1-LV4 has the possibility of being programmed as an anode of a cathode. Accordingly there are a number of LV pacing and sensing vectors that may be tested during implant and follow-up appointments.

The vectors may include a number of bipolar vectors, such as: the combination of LV1 and LV2, with either LV1 or LV2 programmed as the anode and the other programmed as the cathode; the combination of LV2 and LV3, with either LV2 or LV3 programmed as the anode and the other programmed as the cathode; LV3 and LV4 with either LV3 or LV4 programmed as the anode and the other programmed as the cathode; LV1 and LV4 with either LV1 or LV4 programmed as the anode and the other programmed as the cathode; LV2 and LV4, with either LV2 or LV4 programmed as the anode and the other programmed as the cathode; LV1 programmed as a cathode and RVcoil programmed as an anode LV2 programmed as an cathode and RVcoil programmed as an anode; LV3 programmed as an cathode and RVcoil programmed as an anode; or LV4 programmed as a cathode and RVcoil programmed as an anode. The IMD 16 may also be programmed to provide additional vectors that include two or more cathodes and/or two or more anodes. In some examples, one of the LV electrodes is programmed as a cathode and the other three LV electrodes are programmed as anodes. For example, LV1 may be programmed as a cathode with LV2, LV3 and LV4 programmed as anodes. In some examples, IMD 16 may utilize a vector that includes two anodes to two cathodes on the LV lead 20. For example, LV1 and LV 2 may be anodes and LV3 and LV4 may be cathodes. In some examples, the stimulation or sensing may be provided through one or more of LV1-LV4 programmed as cathodes and with the can of IMD 16 functioning as an anode. In some examples, not shown, one of LV1-LV4 may be programmed as a cathode with an RVring electrode on RV lead 18 programmed as an anode. The lead image 140, with the approximate spacing of the lead electrodes depicted, may help a physician or other clinician visualize the vectors resulting from a given electrode combination. This may help the physician to determine which of the numerous choices to test first.

In other examples, not shown, vector options may include a vector between an RV tip electrode and an RV ring electrode or an RV tip electrode and an RV coil electrode. The electrodes of RV may also form vectors with the can of IMD 16, or one or more electrodes on other leads, including LV lead 20. The IMD 16 may include leads placed in areas not shown in FIG. 1, and these lead may also be graphically represented consistent with this disclosure.

Figure 4A:
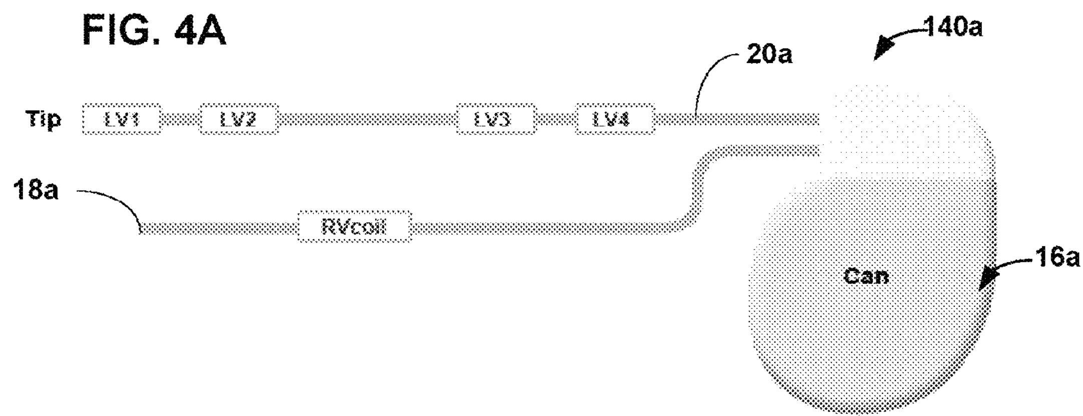
FIGS. 4A-4D are schematic diagrams illustrating example user interfaces including an example lead image.

Programmer 24 may display one of lead images 140 in response to the selection of a left ventricular lead from a list of leads via lead section 116 and/or lead selection screen 118. FIG. 4A depicts Lead image 140*a*, which includes LV lead 20*a* with LV1 and LV2 closely spaced near the tip of LV lead 20*a*. LV3 and LV4, of LV lead 20*a*, are also closely spaced. The space between LV2 and LV3 is larger than the space between LV1 and LV2 and LV3 and LV4. In some examples, including the one shown in image 140*a*, the space between the fourth electrode LV4 and the can may not be accurately shown.

Figure 4B:
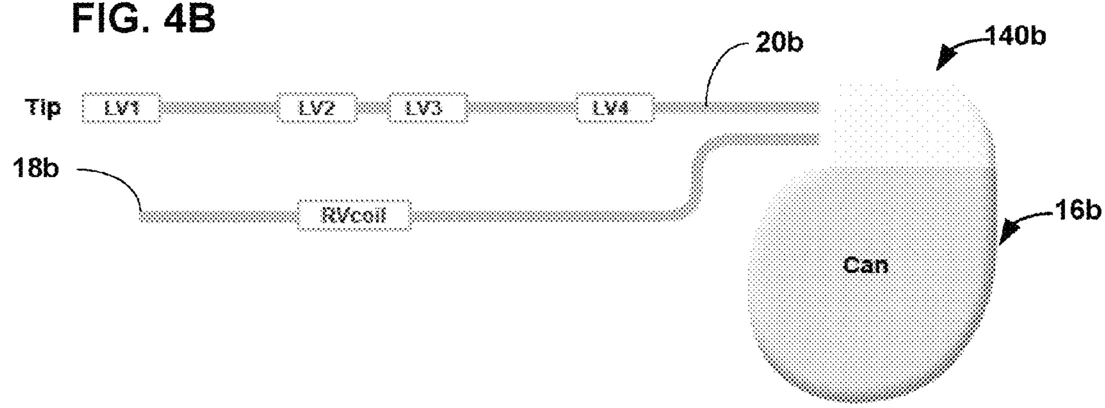

FIG. 4B depicts Lead image 140*b*, which includes LV lead 20*b* with LV1 at the tip of lead 20*b*. LV2 and LV3 are closely spaced together closer to IMD 16*b*. The space between LV1 and LV2 is larger than the spacing between LV2 and LV3. LV4 is closer to the can of IMD 16*b* than LV3 and the space between LV3 and LV4 is greater than the space between LV2 and LV3. In some examples, the spacing depicted in image 140 may be approximate. For example, the relative spacing between LV1, LV2, LV3 and LV4 may be accurate, while the spacing may not exactly equal the actual spacing of the electrodes on the lead 20*b* that has been implanted in patient 14.

Figure 4C:
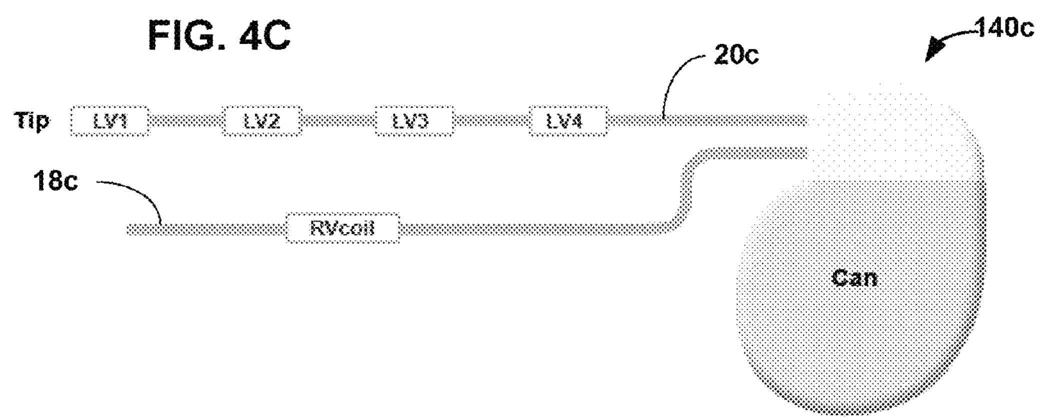

FIG. 4C depicts Lead image 140*c*, which includes LV lead 20 with LV1 at the tip of lead 20*b*. The spacing between LV1, LV2, LV3 and LV4 are approximately equal. In some examples, the relative location of RVcoil on RV lead 18*c* to the electrodes of LV lead 20*c* may approximately equal to the spacing as the leads have been implanted within heart 12.

Figure 4D:
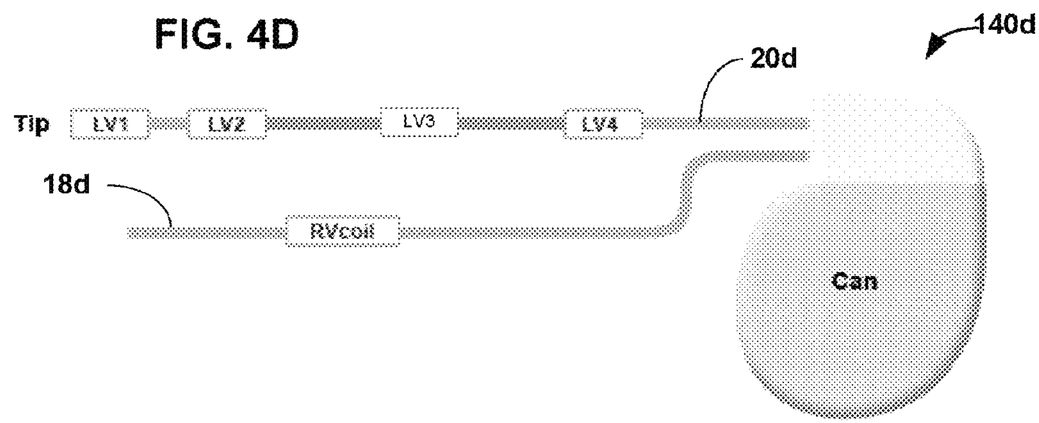

FIG. 4D depicts Lead image 140*d* which includes LV lead 20*d* with LV1 and LV2 closely spaced near the tip of LV lead 20*d*. The spacing between electrodes LV2 and LV3 is approximately equal to the spacing between electrodes LV3 and LV4. In some examples, the spacing depicted in image 140*d* may be approximate. For example, the relative spacing between LV1-LV4 may be accurate while the spacing may not exactly equal the actual spacing of the electrodes on the lead 20D that has been implanted in patient 14. In some examples, the lead may be depicted at multiple of the actual size for ease of visualization.

Figure 5A:
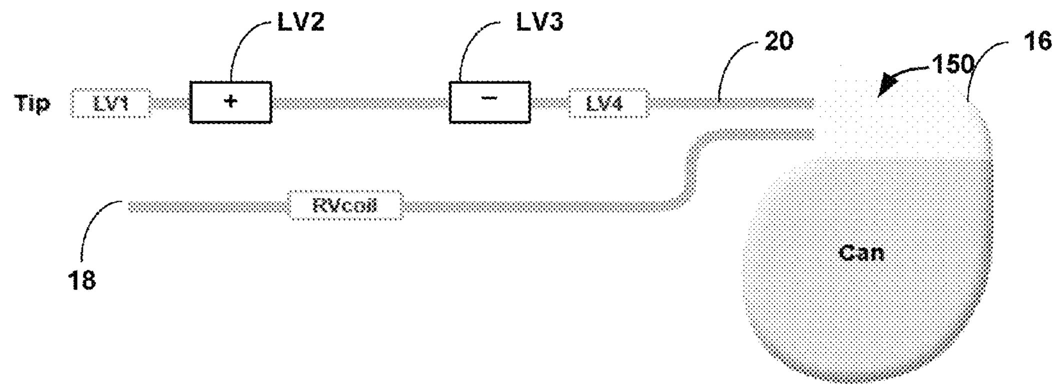
FIG. 5A-5C are schematic diagrams illustrating example graphical user interfaces including an example lead image.

FIG. 5A is as schematic diagram illustrating an example lead image 150 that may be displayed on user interface 98. Lead image 150 includes an IMD 16, a LV lead 20 and a RV lead 18. In the example shown LV lead 20 is a quadripolar lead with electrodes LV1-LV4. In the example shown, electrode LV2 has been selected by a user to be an anode and electrode LV3 has been selected by the user as a cathode. The selection may occur, for example, on parameters screen 130 or tests screen 138. In some examples, the selection may occur when a selected lead image 150 is displayed on a programming interface. Lead image 150 shows the polarities of the electrodes selected by the user.

Figure 5B:
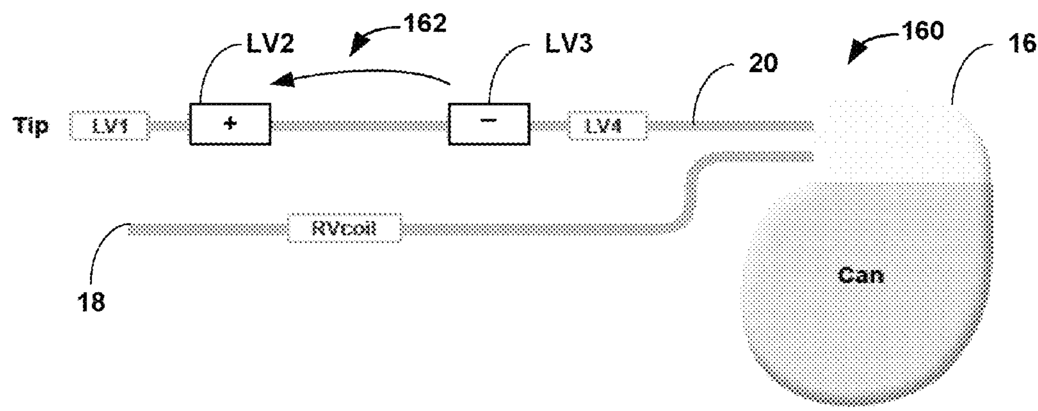

FIG. 5B is a schematic diagram illustrating an example lead image 160 that may be displayed on user interface 98. Lead image 160 includes an IMD 16, a LV lead 20 and a RV lead 18. In the example shown, LV lead 20 is a quadripolar lead with electrodes LV1-LV4. In the example shown, electrode LV2 has been selected by a user to be an anode and electrode LV 3 has been selected by a user to be a cathode. Lead image 160 includes a depiction of the vector 162 created by electrodes LV2 and LV3. This depiction may help a user visualize if the electrodes selected will provide the stimulation desired.

Figure 5C:
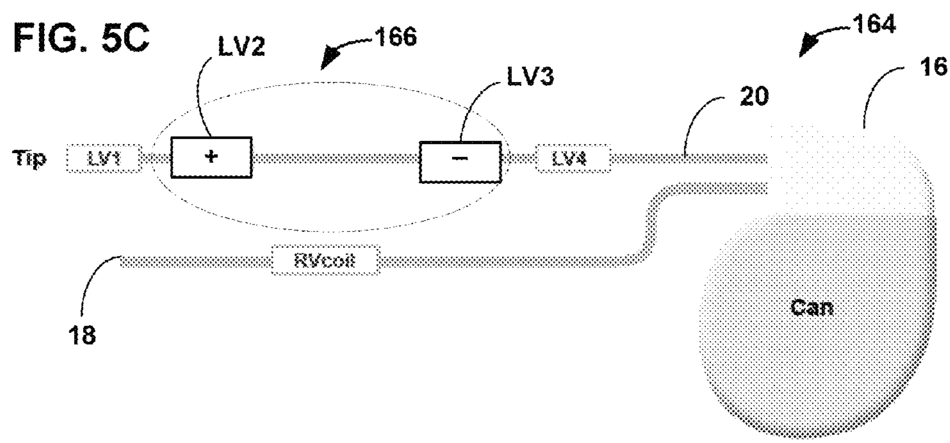

FIG. 5C is a schematic diagram illustrating an example lead image 164 that may be displayed on user interface 98. Lead image 165 includes an IMD 16, a LV lead 20 and a RV lead 18. In the example shown, LV lead 20 is a quadripolar lead with electrodes LV1-LV4. In the example shown, electrode LV2 has been selected by a user to be an anode and electrode LV 3 has been selected by a user to be a cathode. Lead image 164 includes a depiction of an electrode field 166 created by electrodes LV2 and LV3. This depiction may help a user visualize if the electrodes selected will provide the stimulation desired.

Figure 6:
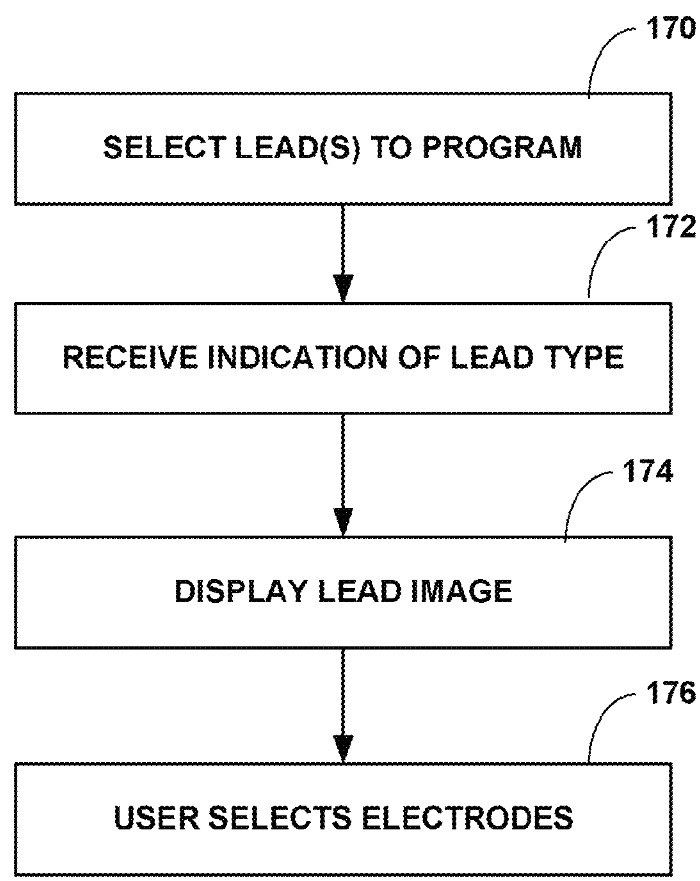
FIG. 6 is a flow diagram illustrating an example method of electrode selection consistent with various examples in this disclosure.

FIG. 6 is a flow diagram illustrating an example method of electrode selection consistent with various examples in this disclosure. A physician or other user may interact with user interface 98 to select lead(s) to program (170). The user may choose to program one or more of the leads that have been implanted in the patient 14 at a time. For example, a physician may desire to visualize both LV lead 20 and RV lead 18 in order to depict the possibility of a vector between one or more of the electrodes of LV lead 20 and an electrode on RV lead 18.

The programmer 24 receives an indication of the lead type (172), e.g., via the user interface. The indication of lead type may be received in the form of a selection made by a user after the user has accessed the options provided by a lead selection screen 118. In some examples, lead selection screen 118 may depict approximate spacings of electrodes from which a user may chose. In some examples, lead selection screen 118 may include thumbnails of lead configurations corresponding to actual leads. In some examples, the thumbnails may be labeled to include a lead model or serial number.

In some examples, programmer 24 may include a scanner, e.g., a barcode scanner, as part of user interface 98. The user may scan the barcode or another identifying from the packaging of the lead that was implanted. The scanner may be able to read a machine readable code. In some examples, the user may scan a barcode on a patient identification that may include information regarding the patient including the lead model number for the implanted lead. In some examples programmer 24 may receive an indication of lead type (172) from IMD 16 via telemetry interface 108.

Based on the indicated lead type, display 100 displays a lead image associated with the indicated lead type (174). In some examples, the processor 88 receives the indication of the lead type (172) form the user interface 98 and accesses memory 90 to retrieve the lead image 92 for display on display 100.

In some examples, the user selects electrodes (176) to be programmed based on the lead image (174) on display 100. In some examples, the selection may be an initial vector to be tested. In some examples, the lead image may be updated to depict the electrodes that have been selected. In some examples, the lead image may be displayed within other display screens, including the tests 128 screen or the parameters 130 screen. This may allow a physician to continually visualize the stimulation that is being provided while changing various parameters or testing the chosen electrode combination.

Figure 7:
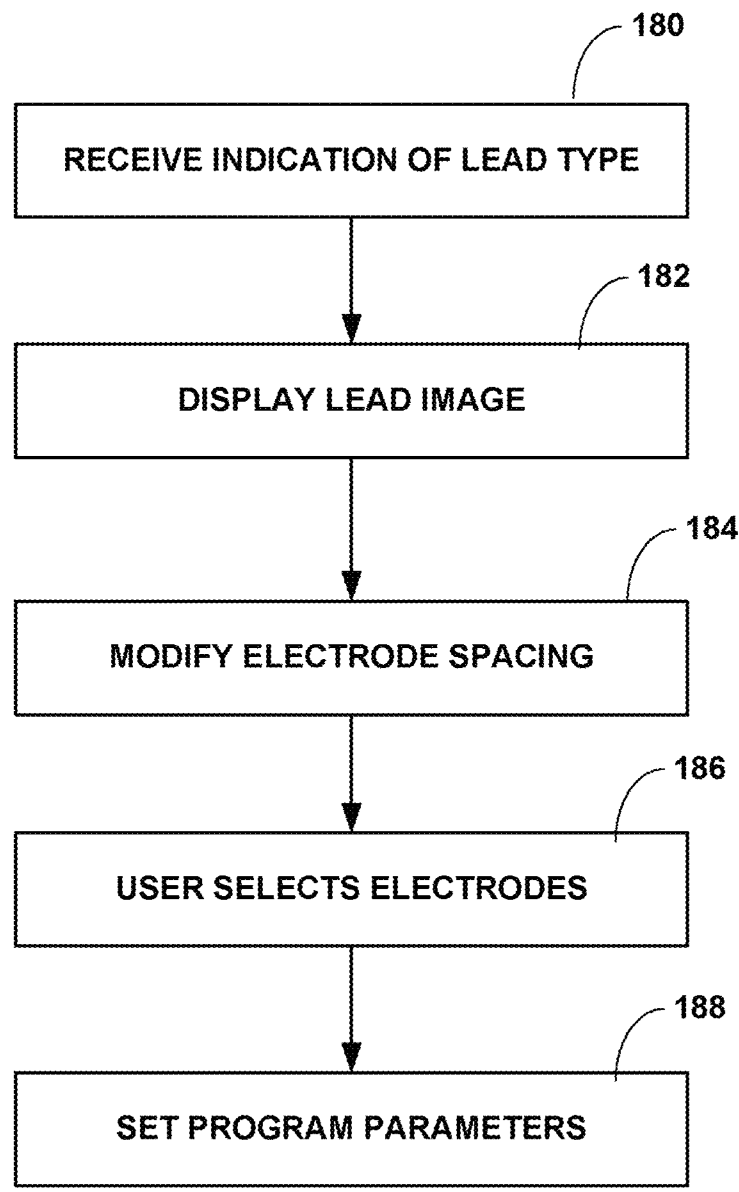
FIG. 7 is a flow diagram illustrating another example method consistent with the present disclosure.

FIG. 7 if a flow diagram illustrating another example method consistent with the present disclosure. An external programmer receives an indication of a lead type (180) that has been implanted in patient 14. As discussed above with respect to FIG. 6, the indication may come from a variety of sources, including user input, user selection from a list or other ordering of images stored within programmer 24 via scanner, or from the IMD 16 itself In response to the indication of lead type (180), processor 88 may retrieve the corresponding lead image for display (182) on user interface 98.

In some examples, after a lead image has been selected based on the indication of lead type and displayed on display 100, a user may modify lead electrode spacing (184). The modification of lead spacing (184) may occur in order to provide a better approximation of the electrode spacing configuration of the lead that has been implanted in patient 14. This may be helpful in instances where the programmer 24 does not include a lead image that exactly corresponds to the lead type indicated or implanted. After a user is satisfied with electrode spacing configuration presented on display 100, a user may select electrodes (186) to test first. In some examples, the selection may be based on previous experience by the user with the same type of lead and electrode spacing configuration. In some examples, the selection may be based on the graphic presented. After a set of electrodes has been chosen, the user sets program parameters (188). In some examples, the user may access previous pacing programs 94 stored within memory 90. In some examples, processor 88 may access the pacing programs 94 and present one or more suggestions based on the electrodes selected by the user. The processes of selecting electrodes and program parameters may be repeated until a combination of electrodes and pacing parameters provides the desired effect.

Various examples have been described. These and other examples are within the scope of the following claims.

The invention claimed is:

1. A system comprising:

a user display;

a memory configured to store a plurality of intracardiac lead images, each of the lead images associated with a respective one of a plurality of lead types, and each of the lead images including a plurality of electrodes spaced according to the spacing of electrodes of the associated lead type, an interface configured to receive an indication of which of the plurality of lead types corresponds to a lead of a patient; and a processor configured to choose the one of the lead images that is associated with the indicated lead type, and provide the chosen image to the user display for display as part of a graphical user interface for programming cardiac stimulation therapy for the patient.

2. The system of claim 1, wherein each of the intracardiac lead images include four electrodes.

3. The system of claim 1, wherein the interface comprises a user interface configured to allow a user to select which of a plurality of intracardiac lead images from a pull-down or a pop-up screen corresponds to the lead of the patient.

4. The system of claim 3, wherein the user interface is configured to present thumbnails of the plurality of intracardiac lead images, and allow the user to select which of a plurality of intracardiac lead images corresponds to the lead of the patient.

5. The system of claim 3, wherein the memory is configured to store each of the lead images in association with a respective one of a plurality of model numbers, and the user interface is configured to allow the user to select which of a plurality of intracardiac lead images corresponds to the lead of the patient based on the model number associated with the lead of the patient.

6. The system of claim 1, wherein each of the plurality of lead types comprises a different electrode spacing configuration.

7. The system of claim 1, wherein the interface comprises a scanner configured to read a machine readable code that indicates which of the plurality of lead types corresponds to the lead of the patient.

8. The system of claim 1, wherein the graphical user interface for programming the cardiac stimulation therapy is further configured to allow the user to select one or more of the plurality of electrodes of the lead image for programming the cardiac stimulation therapy.

9. The system of claim 1, wherein the graphical user interface for programming the cardiac stimulation therapy is further configured to allow the user to modify the spacing of the electrodes of the selected lead image.

10. The system of claim 1, wherein the interface comprises a scanner configured to read a radiofrequency identification tag that indicates which of the plurality of lead types corresponds to the lead of the patient.

* * * * *